United States Patent
Wang et al.

(10) Patent No.: US 7,301,052 B2
(45) Date of Patent: Nov. 27, 2007

(54) PROCESS FOR PRODUCING PERFLUORODIACYL FLUORINATED COMPOUNDS

(75) Inventors: Shu-zhong Wang, Yokohama (JP); Takashi Okazoe, Yokohama (JP); Eisuke Murotani, Yokohama (JP); Kunio Watanabe, Yokohama (JP); Daisuke Shirakawa, Yokohama (JP); Kazuya Oharu, Yokohama (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 11/206,915

(22) Filed: Aug. 19, 2005

(65) Prior Publication Data

US 2006/0030733 A1    Feb. 9, 2006

Related U.S. Application Data

(63) Continuation of application No. PCT/JP2004/001971, filed on Feb. 20, 2004.

(30) Foreign Application Priority Data

Feb. 21, 2003    (JP)    ............................. 2003-044581

(51) Int. Cl.
     *C07C 57/02*    (2006.01)
     *C07C 57/18*    (2006.01)
     *C07C 53/21*    (2006.01)

(52) U.S. Cl. ...................... 562/598; 562/599; 562/605

(58) Field of Classification Search ............... 568/600, 568/604; 562/849, 850, 852, 863
See application file for complete search history.

(56) References Cited

U.S. PATENT DOCUMENTS

| | | | |
|---|---|---|---|
| 3,849,504 A | 11/1974 | Mitsch | |
| 6,858,752 B2 | 2/2005 | Okazoe et al. | |
| 6,894,187 B2 | 5/2005 | Okazoe et al. | |
| 6,956,138 B2 * | 10/2005 | Okazoe et al. | ............... 568/600 |
| 2004/0204618 A1 | 10/2004 | Okazoe et al. | |
| 2004/0254396 A1 | 12/2004 | Okazoe et al. | |
| 2006/0030733 A1 | 2/2006 | Wang et al. | |

FOREIGN PATENT DOCUMENTS

| | | |
|---|---|---|
| GB | 858671 | 1/1961 |
| JP | 52-153897 | 12/1977 |
| JP | 62-64834 | 3/1987 |
| JP | 1-143843 | 6/1989 |
| WO | WO 02/04397 | 1/2002 |

OTHER PUBLICATIONS

U.S. Appl. No. 11/669,989, filed Feb. 1, 2007, Umemura et al.

* cited by examiner

*Primary Examiner*—Karl Puttlitz
(74) *Attorney, Agent, or Firm*—Oblon, Spivak, McClelland, Maier & Neustadt, P.C.

(57) ABSTRACT

The present invention provides a process for producing compounds useful as raw materials for various fluororesins in high yields in few steps from inexpensive and readily available starting materials.

The following compound (1) and the following compound (2) are reacted to form the following compound (3), then the compound (3) is fluorinated in a liquid phase to form the following compound (4), and the ester bonds in the compound (4) are dissociated to form the compound (5), or the compound (5) and the compound (6).

$$HOCH_2\text{-}Q\text{-}O\text{—}(CH_2)_3\text{—}OH, \quad (1)$$

$$CR^BCOX, \quad (2)$$

$$R^BCOOCH_2\text{-}Q\text{-}O\text{—}(CH_2)_3\text{—}OCOR^B, \quad (3)$$

$$R^{BF}COOCF_2\text{-}Q^F\text{-}O\text{—}(CF_2)_3\text{—}OCOR^{BF}, \quad (4)$$

$$FCO\text{-}Q^F\text{-}O\text{—}(CF_2)_2\text{—}COF, \quad (5)$$

$$R^{BF}COF. \quad (6)$$

6 Claims, No Drawings

PROCESS FOR PRODUCING PERFLUORODIACYL FLUORINATED COMPOUNDS

TECHNICAL FIELD

The present invention relates to industrially useful diacyl fluoride compounds having —COF groups at both ends of the molecule. The present invention also relates to novel intermediate useful for production of perfluorodiacyl fluoride compounds useful as precursors of starting materials for fluororesins.

BACKGROUND ART

Perfluorodiacyl fluorides compounds are important precursors for production of monomeric starting materials for heat-resistant and chemical-resistant fluororesins. For example, $CF_2=CF-O(CF_2)_3COOCH_3$, $CF_2=CF-OCF_2CF(CF_3)O(CF_3)_3COOCH_3$, $CF_2=CF-O(CF_2)_3CH_2COOCH_3$ and the like are known as perfluoro(alkyl vinyl ethers) having a carboxyl group in the molecule useful as starting monomers for ion exchange membranes (JP-A-52-153897).

These perfluoro(alkyl vinyl ethers) are produced via perfluoro diacyl fluorides (J. Fluorine Chem., 94, 65-68 (1999)). In particular, the starting monomer for mechanically strong ion exchange membranes, $CF_2=CF-O(CF_2)_3COOCH_3$, is derived from $FCO(CF_2)_2O(CF_2)_2COF$ or $FCOCF(CF_3)O(CF_2)_2COF$.

It is known that diacyl fluorides are generally produced by the following method using iodine and fuming sulfuric acid.

$CF_2=CF_2+I_2 \rightarrow ICF_2CF_2I$ $ICF_2CF_2I+CF_2=CF_2 \rightarrow ICF_2CF_2CF_2CF_2I$ $ICF_2CF_2CF_2CF_2I+SO_3 \rightarrow FCOCF_2CF_2COF$ The present inventors proposed a process for producing perfluoro(diacyl fluorides) from diols by fluorination with fluorine in a liquid phase (liquid phase fluorination) (WO02/4397).

On the other hand, for fluorination of C—H into C—F, fluorination with elemental fluorine is known.

For production of compounds having fluorinated vinyl groups at both ends, it is proposed to treat a compound having $CF_2=CF-$ at one end and having —COF at the other end with chlorine gas or the like to add halogen atoms to $CF_2=CF-$, thermally decompose the terminal —COF into $CF_2=CF-$ and then restore $CF_2=CF-$ by dehalogenation (JP-A-1-143843).

However, conventional processes for producing perfluorodiacyl fluoride compounds from tetrafluoroethylene have a problem of the economical disadvantage of the expensive starting material. Further, there are problems of corrosion of the equipment resulting from use of iodine and fuming sulfuric acid and difficulty in handling the reaction reagents.

DISCLOSURE OF THE INVENTION

It is an object of the present invention to provide a process for producing a perfluorodiacyl fluoride compound from an inexpensive and readily available starting compound in few steps.

It is another object of the present invention to provide a novel intermediate useful for production of a perfluorodiacyl fluoride compound useful as a precursor of a starting material for fluororesins.

Namely, the present invention provides the following.

1. A process for producing a fluorinated compound, which comprises reacting the following compound (1) and the following compound (2) to form the following compound (3), fluorinating the compound (3) in a liquid phase to form the following compound (4), and then dissociating the ester bond in the compound (4) to form a compound (5), or a compound (5) and a compound (6):

$HOCH_2\text{-}Q\text{-}O\text{—}(CH_2)_3\text{—}OH$     (1), $R^BCOX$     (2), $R^BCOOCH_2\text{-}Q\text{-}O\text{—}(CH_2)_3\text{—}OCOR^B$     (3), $R^{BF}COOCF_2\text{-}Q^F\text{-}O\text{—}(CF_2)_3\text{—}OCOR^{BF}$     (4), $FCO\text{-}Q^F\text{-}O\text{—}(CF_2)_2\text{—}COF$     (5), $R^{BF}COF$     (6), wherein
Q: —CH(CH$_3$)— or —CH$_2$CH$_2$—,
$Q^F$: —CF(CF$_3$)— or —CF$_2$CF$_2$—,
X: a halogen atom,
$R^B$: a fluorine-containing monovalent organic group,
$R^{BF}$: the same group as $R^B$, or a group obtained by fluorination of $R^B$.

2. The process according to claim 1, wherein the compound (6) obtained by dissociating the ester bond is used as the compound (2) wherein X is a fluorine atom.

3. The process according to claim 1 or 2, wherein the compound (3) has a fluorine content of from 30 to 76 mass % and a molecular weight of more than 200 and not more than 1000.

4. The process according to claim 1, 2 or 3, wherein Q is —CH$_2$CH$_2$—, and $Q^F$ is —CF$_2$CF$_2$—.

5. A compound selected from the compounds represented by the following formulae:

$R^{BF1}COOCH_2\text{-}Q\text{-}O\text{—}(CH_2)_3\text{—}OCOR^{BF1}$     (3-1)

$R^{BF1}COOCF_2\text{-}Q^F\text{-}O\text{—}(CF_2)_3\text{—}OCOR^{BF1}$     (4-1)

wherein
Q: —CH(CH$_3$)— or —CH$_2$CH$_2$—,
$Q^F$: —CF(CF$_3$)— or —CF$_2$CF$_2$—,
$R^{BF1}$: a perfluoroalkyl group, a perfluoro(mono- or dichloroalkyl) group or a group having an etheric oxygen atom between carbon-carbon atoms in such a group.

6. The compound according to claim 5, wherein $R^{BF1}$ is a $C_{2-20}$ perfluoroalkyl group or a $C_{2-20}$ perfluoroalkyl group having an etheric oxygen atom between a carbon-carbon bond.

7. A compound selected from the compounds represented by the following formulae:

$(CF_3)_2CFCOO(CH_2)_3O(CH_2)_3OCOCF(CF_3)_2$     (3-12), $(CF_3)_2CFCOO(CF_2)_3O(CF_2)_3OCOCF(CF_3)_2$     (4-12), $CF_3(CF_2)_2OCF(CF_3)CF_2OCF(CF_3)COOCH_2CH(CH_3)O(CH_2)_3OCOCF—(CF_3)OCF_2CF(CF_3)O(CF_2)_2CF_3$     (3-13), $CF_3(CF_2)_2OCF(CF_3)CF_2OCF(CF_3)COOCF_2CF(CF_3)O(CF_2)_3OCOCF—(CF_3)OCF_2CF(CF_3)O(CF_2)_2CF_3$     (4-13).

8. A process for producing a compound represented by the following formula (5-4), which comprises reacting a compound represented by the following formula (5-12)

with hexafluoropropylene oxide in the presence of CsF to form a compound represented by the following formula (5-2), pyrolyzing the compound represented by the formula (5-2) into a compound represented by the following formula (5-3), and reacting the compound represented by the formula (5-3) with methanol:

$$FCO(CF_2)_2O(CF_2)_2COF \quad (5\text{-}12),$$

$$FCOCF(CF_3)O(CF_2)_3O(CF_2)_2COF \quad (5\text{-}2),$$

$$CF_2=CFO(CF_2)_3O(CF_2)_2COF \quad (5\text{-}3),$$

$$CF_2=CFO(CF_2)_3O(CF_2)_2COOCH_3 \quad (5\text{-}4).$$

9. The process according to claim 1, wherein the compound represented by the formula (5-12) is obtained by the process as defined in claim 4.

10. A compound selected from the compounds represented by the following formulae:

$$FCOCF(CF_3)O(CF_2)_3O(CF_2)_2COF \quad (5\text{-}2)$$

$$CF_2=CFO(CF_2)_3O(CF_2)_2COF \quad (5\text{-}3)$$

$$CF_2=CFO(CF_2)_3O(CF_2)_2COOCH_3 \quad (5\text{-}4).$$

BEST MODE FOR CARRYING OUT THE INVENTION

Herein, an organic group means a group having carbon atoms as essential constituents and may be saturated or unsaturated. The organic group to be fluorinated may be a group having hydrogen atoms bonded to carbon atoms, a group having carbon-carbon unsaturated bonds or the like. In the present invention, the organic group preferably has a carbon number of from 1 to 20 carbon atoms, particularly from 1 to 10, from the viewpoint of the solubility in the liquid phase to be used for fluorination.

As a monovalent organic group, a monovalent hydrocarbon group, a hetero atom-containing monovalent hydrocarbon group, a halogenated monovalent hydrocarbon group or a halogenated hetero atom-containing monovalent hydrocarbon group is preferred.

As a monovalent hydrocarbon group, a monovalent saturated hydrocarbon group is preferred, and an alkyl group, a cycloalkyl group or a partially cyclic monovalent hydrocarbon group (such as a cycloalkyl group, a cycloalkylalkyl group or a bicycloalkyl group, an alicyclic spiro group, or a group partially having such a group) may be mentioned. An alkyl group is particularly preferred.

Herein, a halogen atom is a fluorine atom, a chlorine atom, a bromine atom, or an iodine atom, preferably a fluorine atom, a chlorine atom, or a bromine atom. A fluorinated group, i.e., a fluoro group, means a group having at least one fluorine atom introduced therein and may or may not have a hydrogen atom. A partially fluorinated group means a group obtained by partially fluorinating the moieties capable of being fluorinated and usually has a hydrogen atom. A perfluoro group means a group obtained by fluorinating substantially all the moieties capable of being fluorinated and usually does not have a hydrogen atom.

According to the present invention, the conventionally hardly available compound (5) can be produced from the compound (1).

The compound represented by the formula (1) include those shown below. These compounds are publicly known or can be synthesized from known compounds by known methods.

$$HO(CH_2)_3O(CH_2)_3OH,$$

$$HOCH_2CH(CH_3)O(CH_2)_3OH$$

In the present invention, first, the compound (1) and the compound (2) are reacted to form the compound (3).

$R^B$ in the compound (2) is a fluorine-containing monovalent organic group, and is the same as $R^{BF}$, which will be mentioned later, or becomes $R^{BF}$ upon fluorination. It is preferred to adjust the structure of $R^B$ so that the resulting compound (3) would have a fluorine content (a fluorine content is the ratio of the fluorine atoms to the molecular weight of a compound) of at least 30 mass %.

$R^B$ preferably has a carbon number of from 2 to 20, particularly from 2 to 10. It is preferred that the carbon number of $R^B$ is at least 2 to facilitate recovery of the compound (6). $R^B$ may be linear, branched, or cyclic or partially cyclic.

As $R^B$, an alkyl group halogenated with a fluorine atom or with a fluorine atom and a chlorine atom, or a group having an etheric oxygen atom between carbon-carbon atoms in such an alkyl group is preferred. As $R^B$, a perfluorinated group, in particular, a perfluoroalkyl group, a perfluoro (mono- or di-chloroalkyl group), or a group having an etheric oxygen atom between carbon-carbon atoms in such a group, is preferred.

When $R^B$ is not any of those mentioned above, $R^B$ may be a group obtained by replacing at least one single bond in the desired $R^{BF}$ with a carbon-carbon double bond or a carbon-carbon triple bond. The carbon atoms constituting a carbon-carbon double bond are preferably bonded to a hydrogen atom or a fluorine atom, in particular, to a hydrogen atom. Through fluorination in a liquid phase, fluorine atoms attach to the unsaturated carbon atoms and replace hydrogen atoms. In such a case, specific examples of $R^B$ include a cyclohexenyl group, a phenyl group, alkenyl groups and alkynyl groups.

In the present invention, $R^B$ being a fluorine-containing group has the advantage of facilitating the after-mentioned continuous process. Further, it is particularly preferred that $R^B$ is the same group as $R^{BF}$ to carry out the after-mentioned continuous process. In this respect, it is particularly preferred that $R^B$ and $R^{BF}$ are perfluorinated monovalent organic groups.

X in the compound (2) is a halogen atom, preferably a chlorine atom or a fluorine atom, and particularly preferably a fluorine atom in order to carry out the after-mentioned continuous process. The compound (2) may be a commercial product or the compound (6) which will be formed by the process of the present invention. The compound (2) is preferred to be the following compound (6) which has $R^{BF}$ as $R^B$, in particular, the compound (6A) which has $R^{BF1}$ as $R^B$.

$$R^{BF}COF \quad (6),$$

$$R^{BF1}COF \quad (6A).$$

wherein $R^{BF1}$ is a perfluoroalkyl group, a perfluoro(mono- or di-chloroalkyl group), or a group having an etheric oxygen atom between carbon-carbon atoms in such a group, such as a perfluoroalkyl group, a perfluoro(partially chlorinated alkyl group), a perfluoro(alkoxyalkyl) group, or a perfluoro(partially chlorinated alkoxyalkyl group), preferably a perfluoroalkyl group or a perfluoroalkyl group having an etheric oxygen atom inserted between carbon-carbon atoms. The carbon numbers of $R^{BF}$ and $R^{BF1}$ are preferably from 2 to 20, in particular from 2 to 10.

Examples of $R^{BF}$ include —$CF_2CF_3$, —$CF_2CF_2CF_3$, —$CF_2CF_2CF_2CF_3$, —$CF_2CF_2Cl$, —$CF_2CF_2Br$, —$CF_2CFClCF_2Cl$, —$CF(CF_3)_2$, —$CF_2CF(CF_3)_2$, —$CF(CF_3)CF_2CF_3$, —$C(CF_3)_3$, —$CF(CF_3)OCF_2CF_2CF_3$, —$CF(CF_3)OCF_2CF_2CFClCF_2Cl$, —$CF(CF_3)OCF_2CF_2Br$, —$CF(CF_3)OCF_2CF(CF_3)O(CF_2)_2CF_3$, and the like.

Specific examples of the compound (2) are the following compounds.

$CF_3CF_2COF$,
$(CF_3)_2CFCOF$,
$CF_2ClCFClCF_2COF$,
$CF_2ClCF_2CFClCOF$,
$CF_3CF_2CF_2OCF(CF_3)COF$,
$CF_2ClCFClCF_2CF_2OCF(CF_3)COF$,
$CF_2ClCF_2COF$,
$CF_2BrCF_2COF$,
$CF_2BrCF_2OCF(CF_3)COF$,
$CF_2ClCFClCF_2CF(CF_3)OCF(CF_3)COF$,
$CF_3CF_2CF_2OCF(CF_3)CF_2OCF(CF_3)COF$,
$CH_3CH_2CH_2OCF(CF_3)COF$,
$CF_3CF_2CF_2OCF_2CF_2COF$.

The compound (2) may be a known compound or obtainable from a known compound by a known method. For example, $CF_3CF_2CF_2OCF(CF_3)COF$ is readily obtained as an intermediate for a perfluoro(alkyl vinyl ether).

The reaction of the compound (1) and the compound (2) can be carried out by known reaction methods under known reaction conditions, for example, under known esterification conditions. The esterification may be carried out in the presence of a solvent (hereinafter referred to as an esterification solvent), but it is preferably carried out in the absence of an esterification solvent in view of volume efficiency.

The esterification solvent, if used, is preferably dichloromethane, chloroform, triethylamine, dichloropentafluoropropane (hereinafter referred to as R-225), or a solvent mixture of triethylamine with tetrahydrofuran. The esterification solvent is preferably used in an amount of from 50 to 500 mass %, in relation to the total amount of the compound (1) and the compound (2).

The reaction of the compound (1) and the compound (2) gives an acid represented by HY. When the compound (2) is a HF-generating compound having a fluorine atom as X, an alkali metal fluoride (preferably NaF or KF) or a trialkylamine may be added to the reaction system as a HF scavenger. It is advisable to use a HF scavenger, when the compound (1) or the compound (2) is acid instable. In the absence of a HF scavenger, it is preferred to carry out the reaction above the vaporization temperature of HF and expel HF with a nitrogen stream from the reaction system. The amount of a HF scavenger is preferably from 1 to 10 times as many moles as that of the compound (2).

In the esterification, the amount of the compound (1) is from 1.5 to 10 times, preferably from 2 to 5 times, as many moles as that of the compound (2). As to the reaction temperature during the esterification, the lower limit is preferably −50° C., and the upper limit is preferably the lower of +100° C. and the boiling point of the solvent. The reaction time can be varied suitably in accordance with the feed rate of the starting materials and the amounts of the compounds to be reacted. The reaction pressure is preferably from 0 to 2 MPa (gauge pressure, the same applies hereinafter).

Because when the compound (3) obtained by the reaction of the compound (1) and the compound (2) has a high fluorine content, it is such a high solubility in the liquid phase used for the fluorination that high yield fluorination is possible with easy control, the fluorine content of the compound (3) is preferably at least 30 mass %. The fluorine content of the compound (3) is appropriately adjusted by varying the structure of $R^B$ as described above, in accordance with the type of the liquid phase, usually to 30-86 mass %, preferably to 30-76 mass %. The compound (3) preferably has a molecular weight larger than 200 and not larger than 1000 so that the liquid phase fluorination in the next step proceeds smoothly without vaporization or decomposition of the compound (3), and the compound (3) is easy to handle and purify.

As the compound (3), the following compound (3-1) is preferred.

$$R^{BF1}COOCH_2\text{-}Q\text{-}O\text{—}(CH_2)_3\text{—}OCOR^{BF1} \qquad (3\text{-}1)$$

wherein

Q: —$CH(CH_3)$ or —$CH_2CH_2$—.

$R^{BF1}$: a perfluoroalkyl group, a perfluoro(mono- or dichloroalkyl group), or a group having an etheric oxygen atom between carbon-carbon atoms in such a group.

$R^{BF1}$ is preferably a perfluoroalkyl group or a perfluoroalkyl group having an etheric oxygen atom inserted between carbon-carbon atoms preferably having a carbon number of from 2 to 20, particularly from 2 to 10.

Specific examples of the compound (3) include the following compounds.

$(CF_3)_2CFCOO(CH_2)_3O(CH_2)_3OCOCF(CF_3)_2$,
$CF_3(CF_2)_2OCF(CF_3)CF_2OCF(CF_3)COOCH_2CH(CH_3)O(CH_2)_3OCOCF$—$(CF_3)OCF_2CF(CF_3)O(CF_2)_2CF_3$.

The crude product containing the compound (3) formed by the reaction of the compound (1) and the compound (2) may be purified, if necessary, or may be used for the next reaction directly. However, it is advisable to purify the crude product so that the fluorination in the next step proceeds smoothly. The crude product may be purified by direct distillation, by treatment with a dilute aqueous alkali followed by partitioning, by extraction with an appropriate organic solvent followed by distillation, or by silica gel column chromatography.

Then, in the present invention, the compound (3) is fluorinated. The fluorination is carried out by liquid phase fluorination in the present invention, though electrolytic fluorination or gas phase fluorination is possible. Liquid phase fluorination is an excellent method which affords the compound (4) in high yields without decomposition of the compound (3).

In liquid phase fluorination, the compound (3) is reacted with fluorine in a liquid phase. The liquid phase may be the reaction substrate or the reaction product, but usually it is preferred to contain a solvent as an essential component. As the fluorine, fluorine gas is preferably used alone or with an inert gas as a diluent. As an inert gas, nitrogen gas or helium gas is preferred. Nitrogen gas is particularly preferred because of its economical advantage. The amount of fluorine gas in relation to nitrogen gas is preferably at least 10 vol %, in particular at least 20 vol %, in terms of efficiency, though there is no particular restrictions.

The fluorination solvent is preferably a solvent which contains no C—H bonds but necessarily contains a C—F bond, in particular a perfluoroalkane or an organic solvent obtained by perfluorination of a known organic solvent having at least one atom selected from the group consisting of chlorine atoms, nitrogen atoms and oxygen atoms in the structure. As the fluorination solvent, a solvent which dissolves the compound (3) well, specifically in an amount of at least 1 mass %, in particular at least 5 mass %, is preferably used.

Examples of the fluorination solvent include the compound (5), the compound (6), which will be described later, perfluoroalkanes (trade names: FC-72 and the like, manufactured by Minn. Mining & Manufacturing Co. (hereinafter referred to as 3M)), perfluoroethers (trade names: FC-75, FC-77 and the like, manufactured by 3M), perfluoropolyethers (trade name: KRYTOX, manufactured by 3M, trade name: FOMBLIN, manufactured by Du Pont, trade name: GALDEN, manufactured by Ausimont, trade name: Demnum, manufactured by DAIKIN, and the like), chlorofluorocarbons, chlorofluoropolyethers, perfluoroalkylamine (such as perfluorotrialkylamines), inert fluids (trade name: Fluorinert, manufactured by 3M) and the like. Particularly preferred is a perfluorotrialkylamine, the compound (5), or the compound (6). In particular, the compound (5) or the compound (6) is preferably used because their use advantageously facilitates post-treatment after the reaction.

The amount of the fluorination solvent is preferably at least 5 times by mass, particularly preferably from 10 to 100 times by mass, that of the compound (3).

The mode of the fluorination is preferably batchwise or continuous. Whether the fluorination is batchwise or continuous, it is preferred to use fluorine gas with an inert gas diluent such as nitrogen gas.

It is preferred to constantly secure an excess of fluorine ($F_2$) over the hydrogen atoms in the compound (1) during the fluorination. The amount of fluorine is preferably at least 1.1 times as many equivalent weights (i.e., at least 1.1 times as many moles), in particular at least 1.5 times as many equivalent weights (i.e., at least 1.5 times as many moles) in view of selectivity. Because it is preferred to always secure an excess of fluorine during the reaction from beginning to end, it is preferred to preliminarily dissolve a sufficient amount of fluorine in the fluorination solvent before loading it into the reactor.

The fluorination is preferably carried out under conditions which prevent cleavage of —$CH_2OCO$—. The lower limit of the reaction temperature is preferably −60° C., and the upper limit is preferably the boiling point of the compound (3). The reaction temperature is preferably between −50° C. and +100° C., in particular between −20° C. and +50° C., in view of yield, selectivity, and ease of industrial operations. The reaction pressure during the fluorination is particularly preferably between atmospheric pressure and 2 MPa in view of yield, selectivity, and ease of industrial operations, though there is no particular restrictions.

Addition of a C—H bond-containing compound to the reaction system, UV irradiation, and the like, especially at a late stage of the fluorination, are preferred to fluorinate the compound (3) in the reaction system efficiently.

The C—H bond-containing compound is preferably an organic compound other than the compound (3), in particular an aromatic hydrocarbon such as benzene or toluene. The amount of a C—H bond-containing compound is preferably from 0.1 to 10 mol %, in particular from 0.1 to 5 mol %, in relation to the hydrogen atoms in the compound (3).

The C—H bond-containing compound is preferably added in the presence of fluorine in the reaction system. When a C—H bond-containing compound is added, it is preferred to apply pressure to the reaction system, preferably at 0.01 to 5 MPa. UV irradiation is preferably carried out for 0.1 to 3 hours using a conventional UV lamp.

The liquid phase fluorination of the compound (3) gives HF as a by-product upon replacement of the hydrogen atoms in the compound (3) by fluorine atoms. To remove the by-product, HF, it is preferred to add a HF scavenger to the reaction system or bring the effluent gas into contact with a HF scavenger at the gas outlet of the reactor. As the HF scavenger, those previously mentioned may be used, and NaF is preferred.

When the HF scavenger added to the reaction system, the amount of the HF scavenger is preferably from 1 to 20 times, in particular from 1 to 5 times, as many moles as the total amount of the hydrogen atoms in the compound (3). When a HF scavenger is provided at the gas outlet of the reactor, it is preferred to arrange (a) a cooler (preferably at 10° C. to room temperature, particularly at about 20° C.), (b) a packed bed of NaF pellets and (c) a cooler (preferably at −78° C. to +10° C., in particular at −30° C. to 0° C.) in series in the order of (a)-(b)-(c). Further, a liquid recirculation line may be provided to the cooler (c) to return the liquid condensate to the reactor.

The fluorination of the compound (3) gives the compound (4). $R^{BF}$ in the compound (4) is a fluorine-containing organic group which may be the same as or different from $R^B$, and, when different, it is a group obtained by fluorination of $R^B$. For example, when $R^B$ in the compound (3) is a hydrogen-containing group, $R^{BF}$ resulting from replacement of the hydrogen atoms therein with fluorine atoms is different from $R^B$. Meanwhile, when $R^B$ is a group having no hydrogen atoms (for example, a perhalogenated group such as perfluorinated group), $R^{BF}$ is the same as $R^B$. $R^{BF}$ is preferably a perfluorinated group.

Specific examples of $R^{BF}$ are the same as those mentioned for a perfluorinated group as $R^B$.

$Q^F$ in the compound (4) is a group obtained by perfluorinating Q. When Q is —$CH_2CH_2$—, $Q^F$ is —$CF_2CF_2$—, and when Q is —$CH(CH_3)$—, $Q^F$ is —$CF(CF_3)$—.

As the compound (4), the following compound (4-1) is preferred.

$$R^{BF1}COOCF_2\text{-}Q^F\text{-}O\text{—}(CF_2)_3\text{—}OCOR^{BF1} \qquad (4\text{-}1)$$

wherein $Q^F$: —$CF(CF_3)$— or —$CF_2CF_2$—, $R^{BF1}$: a perfluoroalkyl group, a perfluoro(mono- or dichloroalkyl group), or a group having an etheric oxygen atom between carbon-carbon atoms in such a group. As $R^{BF1}$, a perfluoroalkyl group or a perfluoroalkyl group having an etheric oxygen atom inserted between carbon-carbon atoms, preferably having a carbon number of 2 to 20, in particular from 2 to 10, is preferred.

As specific examples of the compound (4), the following compounds may be mentioned.

$(CF_3)_2CFCOO(CF_2)_3O(CF_2)_3OCOCF(CF_3)_2$,
$CF_3(CF_2)_2OCF(CF_3)CF_2OCF(CF_3)COOCF_2CF(CF_3)O$
$(CF_2)_3OCOCF—(CF_3)OCF_2CF(CF_3)OCF_2CF_2CF_3$.

The crude fluorination product containing the compound (4) may be used for the next step directly, or purified to a high purity, for example, by directly distilling the crude product under ordinary pressure or reduced pressure.

In the present invention, then, the ester bonds in the compound (4) are dissociated to form the compound (5), or the compound (5) and the compound (6). Upon the dissociation of the ester, a —$CF_2OCO$— bond cleaves, each forming two —COF groups.

The dissociation of the ester bond in the compound (4) is preferably carried out by pyrolysis or in the presence of a nucleophile or an electrophile. As a result of the dissociation, the compound (5) having —COF at both ends is formed, usually together with the compound (6).

Pyrolysis is carried out by heating the compound (4). The reaction system for the pyrolysis is preferably selected in view of the boiling point and stability of the compound (4).

For example, when the compound (4) is volatile, gas phase pyrolysis may be used by dissociating the compound (4) continuously in a gas phase and condensing and collecting the effluent gas containing the compound (5).

The reaction temperature for gas phase pyrolysis is preferably from 50 to 350° C., particularly from 50 to 300° C., particularly preferably from 150 to 250° C. In the gas phase pyrolysis, an inert gas which does not participate in the reaction may be added to the reaction system. As the inert gas, nitrogen, carbon dioxide, or the like may be mentioned. An inert gas is preferably added in an amount of from 0.01 to 50 vol %, in relation to the compound (4). If the amount of an inert gas is too large, the recovery of the dissociation product can be low.

Meanwhile, if the compound (4) is nonvolatile, liquid phase pyrolysis is preferably used by heating the compound (4) in a liquid state in a reactor. In this case, the reaction pressure is not particularly restricted. Because the product containing the compound (5) usually has a lower boiling point, the product is preferably withdrawn continuously as a vapor by reactive distillation. The product may be withdrawn from the reactor all at once after completion of heating. The reaction temperature for the liquid phase pyrolysis is preferably from 50 to 300° C., particularly preferably from 100 to 250° C.

The liquid phase pyrolysis may be carried out in the absence of a solvent or in the presence of a solvent (hereinafter referred to as a dissociation solvent), but preferably in the absence of a solvent or in the presence of the same solvent as used in the liquid phase fluorination. The dissociation solvent in not particularly restricted so long as it is unreactive and compatible with the compound (4) and unreactive with the compound (5). As the dissociation solvent, it is preferred to choose a solvent which is easy to separate by purification. Specific preferable examples of the dissociation solvent include inert solvents such as perfluorotrialkylamines and perfluoronaphthalene, and high-boiling chlorofluorocarbons called chlorotrifluoroethylene oligomers. The amount of the dissociation solvent to be used is preferably from 0.10 to 10 times by mass that of the compound (4).

When the ester bonds are dissociated through reaction with a nucleophile or electrophile in a liquid phase, the reaction may be carried out in the absence of a solvent or in the presence of a dissociation solvent, but preferably in the present of a solvent or in the presence of the same solvent as in the liquid fluorination. The nucleophile is preferably F⁻, particularly preferably F⁻ derived from an alkali metal fluoride. The alkali metal fluoride is preferably NaF, NaHF₂, KF, or CsF. Among them, NaF is particularly preferred from an economical aspect. It is particularly preferred to carry out the dissociation of the ester bonds in the absence of a solvent, because the compound (4) itself serves as the solvent, so that it is not necessary to separate the solvent from the reaction product.

When F⁻ is used as a nucleophile in the dissociation of the ester bonds, F⁻ nucleophilically attaches to the carbonyl groups in the ester bonds in the compound (4) to form the compound (5), and $R^{BF}CF_2O^-$ is released. $R^{BF}CF_2O^-$ further releases F⁻ to give the compound (6). The released F⁻ reacts with another molecule of the compound (4) similarly. Therefore, the nucleophile to be used at the initial sage of the reaction may be in a catalytic amount or in an excess amount. The amount of the nucleophile such as F⁻ is preferably from 1 to 500 mol %, particularly from 1 to 100 mol %, especially preferably from 5 to 50 mol %, in relation to the compound (4). The reaction temperature is preferably from −30° C. to the boiling point of the solvent or the boiling point of the compound (4), particularly preferably from −20° C. to 250° C. The liquid phase pyrolysis is preferably carried out with distillation in a reactor equipped with a distillation column.

As the compound (5), the following compounds may be mentioned.

FCO(CF₂)₂O(CF₂)₂COF,
FCOCF(CF₃)OCF₂CF₂COF.

Specific examples of the compound (6) include the following compounds.

CF₃CF₂COF,
(CF₃)₂CFCOF,
CF₂ClCFClCF₂COF,
CF₂ClCF₂CFClCOF,
CF₃CF₂CF₂OCF(CF₃)COF,
CF₂ClCFClCF₂CF₂OCF(CF₃)COF,
CF₂ClCF₂COF,
CF₂BrCF₂COF,
CF₂BrCF₂OCF(CF₃)COF,
CF₂ClCFClCF₂CF(CF₃)OCF(CF₃)COF,
CF₃CF₂CF₂OCF(CF₃)CF₂OCF(CF₃)COF,
CF₃CF₂CF₂OCF₂CF₂COF.

An embodiment of the process of the present invention wherein $R^B$ and $R^{BF}$ are (CF₃)₂CF— or CF₃(CF₂)₂OCF(CF₃)CF₂OCF(CF₃)— is preferred.

The following compounds corresponding to the compounds (3) and the compounds (4) wherein $R^B$ and $R^{BF}$ are the above-mentioned groups are novel compounds.

(CF₃)₂CFCOO(CH₂)₃O(CH₂)₃OCOCF(CF₃)₂     (3-12), (CF₃)₂CFCOO(CF₂)₃O(CF₂)₃OCOCF(CF₃)₂     (4-12),

CF₃(CF₂)₂OCF(CF₃)CF₂OCF(CF₃)COOCH₂CH(CH₃)O(CH₂)₃OCOCF—(CF₃)OCF₂CF(CF₃)O(CF₂)₂CF₃     (3-13),

CF₃(CF₂)₂OCF(CF₃)CF₂OCF(CF₃)COOCF₂CF(CF₃)O(CF₂)₃OCOCF—(CF₃)OCF₂CF(CF₃)O(CF₂)₂CF₃     (4-13).

The terminal —CF₂COF and —CF(CF₃)COF ends of the compound (5) obtained in the present invention can be converted to —CF═CF₂ pyrolytically by conventional methods (Methods of Organic Chemistry, 4, Vol. 10b, Part 1, p. 703 and J. Fluorine Chem., 94, 65-68 (1999). J. Org. Chem., 34, 1841 (1969)).

For example, the compound (5) can be pyrolytically converted to the following compound (7) having two fluorinated vinyl groups.

CF₂═CF—O—CF═CF₂     (7)

The conversion of the terminal —COF groups in the compound (5) to —COOR (wherein R is a monovalent organic group, preferably an alkyl group, particularly preferably a methyl group) followed by pyrolysis affords a compound represented by the formula CF₂═CFO(CF₂)₂COOCH₃, which is useful as a starting material for fluororesins.

The compound (5) can be converted to a useful starting material for fluororesins such as CF₂═CFO(CF₂)₃O(CF₂)₂COOCH₃ (the following compound (5-4)) by reacting either terminal —COF group of the compound (5) with hexafluoropropylene oxides (HFPO) and then converting it to —COOR in the same manner as mentioned above. Fluororesins obtained from the compound (5-4) are useful as fluororesins for ion exchange membranes, obtainable by a more economically and industrially advantageous process, and more durable than conventional fluororesins.

The above-mentioned process comprises, for example, reacting the following compound (5-12) with HFPO in the presence of CsF to form the following compound (5-2), pyrolyzing the compound (5-2) into the following compound (5-3) and reacting the compound (5-3) with methanol to form the compound (5-4).

$$FCO(CF_2)_2O(CF_2)_2COF \quad (5\text{-}12)$$

$$FCOCF(CF_3)O(CF_2)_3O(CF_2)_2COF \quad (5\text{-}2),$$

$$CF_2{=}CFO(CF_2)_3O(CF_2)_2COF \quad (5\text{-}3),$$

$$CF_2{=}CFO(CF_2)_3O(CF_2)_2COOCH_3 \quad (5\text{-}4).$$

The compound (5-2), the compound (5-3), and the compound (5-4) in the above-mentioned process have not been disclosed in any literature and are novel compounds. A fluororesin containing repeating units derived from the compound (5-4) can have excellent durability.

In the process of the present invention, when $R^B$ and $R^{BF}$ have the same structure, the compound (6) is the same as the compound (2). In this case, the compound (6) may be recovered and used as the compound (2) to be reacted with the compound (1) to produce the compound (5). Such a process can be carried out continuously and, therefore, is more efficient. When the compound (6) is recovered, the carbon number of $R^{BF}$ is preferably at least 2, particularly from 2 to 20, particularly preferably from 4 to 10.

According to the process of the present invention, the diacyl fluoride compound (5) can be produced from an inexpensively available starting material in few steps in a high yield, and various compounds having a polymerizable fluorinated vinyl group can be produced by virtue of the reactivity of the terminal —COF groups. Further, according to the present invention, novel compounds useful for production of the diacyl fluoride compound (5) can be obtained.

EXAMPLES

Now, the present invention will be described in further details with reference to Examples. However, the present invention is by no means restricted thereto. Hereinafter, gas chromatography is abbreviated as GC. A purity calculated from a relative GC peak area is referred to as a GC purity, a purity calculated from the relative peak area in an NMR spectrum is referred to as an NMR purity, and a yield determined by NMR is referred to as an NMR yield. For quantitative analysis by $^{19}$F-NMR, perfluorobenzene was used as the internal standard sample. Tetramethylsilane is referred to as TMS. The NMR spectra data are shown as apparent ranges of chemical shifts.

Example 1

Example 1-1 Preparation of $(CF_3)_2CFCOO(CH_2)_3O(CH_2)_3OCOCF(CF_3)_2$ $HO(CH_2)_3O(CH_2)_3OH$ (10 g) was loaded into an autoclave and stirred in a sealed state, and $FCOCF(CF_3)_2$ (36.95 g) was fed over 7 hours at room temperature with occasional pauses for bubbling with nitrogen gas under unsealed conditions. After the feeding, the reaction solution was stirred at room temperature for 1 hour and bubbled with nitrogen gas under unsealed conditions. The reaction solution was neutralized with saturated aqueous $NaHCO_3$ (100 mL) and extracted with R-225 (100 mL) in twice. The organic phase was washed with saturated aqueous $NaHCO_3$ (50 mL) and further with saturated aqueous NaCl (50 mL). The organic phase was dried over magnesium sulfate and filtered to give 36.13 g of a crude liquid.

Part of the crude liquid (9.07 g) was purified by silica gel column chromatography (developing solvent: R-225) to give the title compound (8.02 g) which was identified by the following NMR spectrum, in an NMR yield of 81% with a GC purity of 98%.

NMR Spectrum of the Product $^1$H-NMR(300.4 MHz, solvent: CDCl$_3$, standard: TMS) δ (ppm): 1.99(m,4H), 3.48(t,4H), 4.15(t,4H).

$^{19}$F-NMR(282.65 MHz, solvent: CDCl$_3$, standard: CFCl$_3$) δ (ppm): −74.4(12F), −180.8(2F).

Example 1-2 Preparation of $(CF_3)_2CFCOO(CF_2)_3O(CF_2)_3OCOCF(CF_3)_2$ 1,1,2-Trichloro-1,2,2-trifluoroethane (hereinafter referred to as R-113) (323 g) was loaded into a 500 mL nickel autoclave and stirred at 25° C. To the gas outlet of the autoclave, a cooler maintained at −10° C. was provided. Nitrogen gas was introduced for 1 hour, and fluorine gas diluted to 20 vol % with nitrogen gas (hereinafter referred to 20% fluorine gas) was introduced at a rate of 13.22 L/h for 1 hour.

Then, while 20% fluorine gas was introduced at the same flow rate, $(CF_3)_2CFCOO(CH_2)_3O(CH_2)_3OCOCF(CF_3)_2$ (5 g) prepared in Example 1-1 dissolved in R-113 (50 g) was injected over 1.5 hours. The temperature in the reactor was raised from 25° C. to 40° C., while the internal pressure was kept at 0.15 MPa, and 0.01 g/mL benzene solution in R-113 (9 mL) was injected while 20% fluorine gas was introduced at the same flow rate. 15 minutes later, the same benzene solution (6 mL) was injected, while the temperature was maintained at 40° C. The same benzene solution (6 mL) was further injected after another 15 minutes. 0.215 g of benzene and 21 mL of R-113 were injected in total. 20% Fluorine gas was introduced at the same flow rate for 1 hour, and then nitrogen gas was introduced for 1 hour. The title compound dominated in the product, and the NMR yield was 92%. The product gave the following NMR spectrum data.

$^{19}$F-NMR(376.0 MHz, solvent: CDCl$_3$, standard: CFCl$_3$) δ (ppm): −74.6(12F), −83.8(4F), −86.8(4F), −129.4(4F) −181.6(2F).

Example 1-3 Preparation of $FCO(CF_2)_2O(CF_2)_2COF$ by Dissociation of Ester Bonds in a Liquid Phase A 7:5 (molar ratio) mixture (342 g) of $(CF_3)_2CFCOO(CF_2)_3O(CF_2)_3OCOCF(CF_3)_2$ prepared in Example 1-2 and $CF_3(CF_2)_2OCF(CF_3)CF_2OCF(CF_3)COF$ was loaded into a flask together with NaF powder (4.8 g) and heated at 80° C. on an oil bath with vigorous stirring for 3 hours. After installation of distillation equipment, the distillate having a boiling point of 100° C. or below was collected as a liquid sample (75 g). The title compound was identified as the main component by NMR spectrum analysis. The NMR yield of the title compound was 34%.

$^{19}$F-NMR(282.65 MHz, solvent: CDCl$_3$, standard CFCl$_3$) δ (ppm): 24.8(2F), −85.8(4F), −121.6(4F).

Example 1-4 Preparation of FCOCF(CF$_3$)O(CF$_2$)$_3$O (CF$_2$)$_2$COF by Addition of HFPO Dry CsF (30 g) was loaded into a 2 L hastelloy C autoclave, and the reactor was degassed. FCO(CF$_2$)$_2$O (CF$_2$)$_2$ COF (1245 g) prepared in Example 1-3 and tetraglyme (153 g) were loaded into the reactor, and the reactor was cooled to −20° C. HFPO (674 g) was fed continuously with feed control to maintain the temperature at 0° C. or below. After the reaction, the fluorocarbon layer (lower layer) (1836 g) was collected by using a separatory funnel. The compound in the fluorocarbon layer was identified as FCOCF(CF$_3$)O(CF$_2$)$_3$O(CF$_2$)$_2$COF by $^{19}$F-NMR and GC-Mass spectrum (EI detection) analysis.

$^{19}$F-NMR(282.7 MHz, solvent: CDCl$_3$, standard: CFCl$_3$) δ (ppm): 26.4(1F), 24.6(1F), −78.5(1F), −81.6(3F), −82.2 (2F), −85.0(2F), −86.0(1F), −120.7(2F), −128.3(2F), −130.1 (1F). EI-MS; 313, 166.

Example 1-5 Preparation of CF$_2$=CFO(CF$_2$)$_3$O (CF$_2$)$_2$COF by Pyrolysis of FCOCF(CF$_3$)O(CF$_2$)$_3$O (CF$_2$)$_2$COF A tubular fluidized bed reactor (inner diameter 100 mm, length 500 mm, made of SUS) packed with glass beads (3500 ml, mean particle size 160 μm, specific gravity 1.47 g/mL) was heated with a tubular mantle heater. A glass trap cooled with dry ice was provided at the outlet of the tubular reactor.

Then, nitrogen gas (14.7 mol/h), the starting material FCOCF(CF$_3$)O(CF$_2$)$_3$O(CF$_2$)$_2$COF (0.94 mol/h, 447 g/h) prepared in Example 1-4 and distilled water (1.5 g/h) were mixed and heated to 150° C. and vaporized, and the resulting gas mixture was introduced to the tubular reactor from the bottom and brought into contact with the glass beads to cause reaction. After 1788 g of the starting material was fed during 4 hours of the reaction, the feeding of the starting material and distilled water was stopped, while nitrogen only was fed, for blank heating of glass beads. After the blank heating, the liquid distillate (1364 g) collected in the glass trap was recovered. Analysis of the liquid by gas chromatography, $^{19}$F-NMR and EI-MS revealed formation of the title compound in a yield of 71.0%.

$^{19}$F-NMR(282.7 MHz, solvent: CDCl$_3$, standard: CFCl$_3$) δ (ppm): 24.6(1F), −83.4(2F), −85.2(2F), −85.3(2F), −112.5 (1F), −120.8(2F), −121.0(1F), −128.5(2F), −134.7(1F). EI-MS; 410(M$^+$).

Example 1-6 Preparation of CF$_2$=CFO(CF$_2$)$_3$O (CF$_2$)$_2$COOCH$_3$ by Addition of Methanol to CF$_2$=CFO(CF$_2$)$_3$O(CF$_2$)$_2$COF CF$_2$=CFO(CF$_2$)$_3$O(CF$_2$)$_2$COF (2200 g) prepared in the same manner as in Example 1-5 was loaded into a 2 L hastelloy C autoclave, and methanol (190 g) was introduced gradually while the inside of the reactor was maintained at 30° C. or below at ordinary temperature by cooling the reactor. At the same time, the reaction solution was bubbled with nitrogen gas with sufficient stirring, to expel HF resulting from the reaction. After all the methanol had been fed, the reaction solution was bubbled with nitrogen gas at 30° C. for another 12 hours, and as a result, 2260 g of the product was obtained. The product was identified as CF$_2$=CFO(CF$_2$)$_3$O(CF$_2$)$_2$COOCH$_3$ by analysis by $^{19}$F-NMR, $^{13}$C-NMR, C—F 2D NMR and GC-Mass spectrometry (EI detection, CI detection).

$^{19}$F-NMR(282.7 MHz: solvent: CDCl$_3$: standard: CFCl$_3$) δ (ppm): −84.1(2F, tt, 12.2 Hz, 6.1 Hz), −85.7(2F,m), −85.9(2F, t, 12.2 Hz), −114.3(1F, dd, 85 Hz, 66 Hz), −122.0(2F,s), −122.3(1F, ddt, 113 Hz, 85 Hz, 6 Hz), −129.5 (2F,s), −135.9(1F, ddt, 113 Hz, 66 Hz, 6 Hz).

$^{13}$C-NMR(282.7 MHz, solvent: CDCl$_3$, standard: CDCl$_3$) δ (ppm): 54.1, 106.5, 107.2, 115.7, 116.2, 116.3, 129.8, 147.4, 158.9. C—F 2D NMR was also used for assignment of each peak. CI-MS (methane); 423 (M+1). EI-MS; 325 (M-CF$_2$CFO).

Example 2

Example 2-1 Preparation of TsOCH(CH$_3$)CH$_2$OC (CH$_3$)$_3$ (Wherein and Hereinafter Ts is a p-toluenesulfonyl Group)

HOCH(CH$_3$)CH$_2$OC(CH$_3$)$_3$ (400.54 g) was loaded into a four-necked flask and stirred with pyridine (1000 mL). While the reaction solution was cooled on an ice bath to keep the temperature in the reactor at 5° C., p-toluenesulfonyl chloride (605.82 g) was added gradually over 2 hours. After addition of water (1 L), the reaction solution was extracted with chloroform (500 mL) twice, and the separated liquid layers were collected. The organic layer was washed with water (1 L), then with NaHCO$_3$ (1 L) twice and with water (1 L) 7 times, dried over magnesium sulfate and filtered. The filtrate was concentrated with an evaporator to give the title compound (909.93 g) containing about 9% of pyridine. The NMR spectrum data of the product were as follows.

$^1$H-NMR(300.4 MHz, solvent: CDCl$_3$, standard: TMS) δ (ppm): 1.03(s,9H), 1.33(d,J=6.3 Hz, 3H), 2.43(s,3H), 3.34 (m,2H), 4.58(m,1H), 7.31(m,2H), 7.81(m,2H).

Example 2-2 Preparation of HO(CH$_2$)$_3$OCH(CH$_3$) CH$_2$OC(CH$_3$)$_3$

Potassium hydroxide (274.27 g) and HO(CH$_2$)$_3$OH (371.93 g) were added to dioxane (3 L), and then TsOCH (CH$_3$)CH$_2$OC(CH$_3$)$_3$ (700 g) prepared in Example 2-1 was added gradually. The reaction solution was refluxed with heating for 16 hours, allowed to cool, and poured onto ice (500 g), neutralized with 2 N hydrochloric acid, concentrated and filtered to remove the precipitated salt. The filtrate was extracted with dichloromethane (250 mL), and the organic layer was washed with water (500 mL) repeatedly 17 times. The organic layer was dried over magnesium sulfate and filtered, and the filtrate was concentrated with an evaporator, and the concentrate was purified by silica gel chromatography to give the title compound (203.77 g). The NMR spectrum data of the product were as follows.

$^1$H-NMR(300.4 MHz, solvent: CDCl$_3$, standard: TMS) δ (ppm): 1.15(d,J=6.2 Hz, 3H), 1.19(s, 9H), 1.81(m, 2H), 3.2(bs, 1H), 3.24-3.36(m, 2H), 3.54-3.68(m, 2H), 3.75-3.86 (m, 3H).

Example 2-3 Preparation of HO(CH$_2$)$_3$OCH(CH$_3$) CH$_2$OH

HO(CH$_2$)$_3$OCH(CH$_3$)CH$_2$OC(CH$_3$)$_3$ (203.39 g) prepared in Example 2-2 was loaded into a round-bottomed flask and stirred with 5 N hydrochloric acid (1 L) at room temperature for 43 hours. The reaction solution was concentrated with an evaporator, and then, after addition of toluene, concentrated again with an evaporator to give the title compound (131 g). The NMR spectrum data of the product were as follows.

$^1$H-NMR(300.4 MHz, solvent: CDCl$_3$: standard: TMS) δ (ppm): 1.12(d,J=6.2 Hz, 3H), 1.85(m,2H), 3.45(m,1H), 3.54-3.88(m,6H), 4.55(bs,2H).

Example 2-4 Preparation of CF$_3$(CF$_2$)$_2$OCF(CF$_3$)CF$_2$OCF(CF$_3$)COOCH$_2$CH(CH$_3$)O(CH$_2$)$_3$OCOCF(CF$_3$)—OCF$_2$CF(CF$_3$)O(CF$_2$)$_2$CF$_3$ CF$_3$(CF$_2$)$_2$OCF(CF$_3$)CF$_2$OCF(CF$_3$)COF (120.69 g) was loaded into an autoclave and stirred under a nitrogen stream, and HO(CH$_2$)$_3$OCH(CH$_3$)CH$_2$OH (15.1 g) prepared in Example 2-3 was fed over 2 hours, while the temperature in the autoclave was maintained at 30° C. or below. Then, the reaction solution was stirred at room temperature under a nitrogen stream overnight and poured onto saturated aqueous NaHCO$_3$ (500 mL) with ice.

The resulting crude solution was extracted with R-225 (250 mL) twice, and the lower layer was washed with saturated aqueous NaHCO$_3$ (250 mL) twice, and then with saturated aqueous NaCl (250 mL) twice, dried over magnesium sulfate, filtered and concentrated with an evaporator to give a crude solution. The crude solution was purified by silica gel column chromatography (developing solvent: hexane/R-225=3:2 (volume ratio)) to give the title compound (86.3 g) with a GC purity of 75% in an NMR yield of 75%. The NMR spectrum data of the product were as follows.

$^1$H-NMR(300.4 MHz, solvent: CDCl$_3$, standard: TMS) δ (ppm): 1.18(d,J=6.3 Hz, 3H), 1.90-1.98(m,2H), 3.45-3.71 (m,3H), 4.18-4.53(m,4H).

$^{19}$F-NMR(282.7 MHz, solvent: CDCl$_3$, standard: CFCl$_3$) δ (ppm): −79(2F), −80.2(6F), −81(10F), −82(6F), −85(2F), −129.5(4F), −131(2F), −145(2F).

Example 2-5 Preparation of CF$_3$(CF$_2$)$_2$OCF(CF$_3$)CF$_2$OCF(CF$_3$)COOCF$_2$CF(CF$_3$)O(CF$_2$)$_3$OCOCF(CF$_3$)OCF$_2$CF(CF$_3$)O(CF$_2$)$_2$CF$_3$ R-113 (323 g) was loaded into a 500 mL nickel autoclave and stirred at 25° C. at the gas outlet of the autoclave, a cooler maintained at 20° C., NaF pellets and a cooler maintained at −10° C. were arranged in series. Nitrogen gas was introduced for 1 hour, and 20% fluorine gas was introduced at a rate of 90 L/h for 1 hour.

Then, while 20% fluorine gas was introduced at the same flow rate, CF$_3$(CF$_2$)$_2$OCF(CF$_3$)CF$_2$OCF(CF$_3$)COOCH$_2$CH(CH$_3$)O)CH$_2$)$_3$OCOCF(CF$_3$)OCF$_2$CF(CF$_3$)O(CF$_2$)$_2$CF$_3$ (25 g) prepared in Example 2-4 dissolved in R-113 (250 g) was injected over 7.0 hours. The temperature in the reactor was raised from 25° C. to 40° C., while the internal pressure was kept at 0.15 MPa, and 0.01 g/mL benzene solution in R-113 (9 mL) was injected while 20% fluorine gas was introduced at the same flow rate. After the injection, the reaction solution was stirred at 40° C. for 15 minutes, with the benzene inlet closed. Then, while the internal pressure and the temperature in the reactor were kept at 0.15 MPa and 40° C., respectively, the same benzene solution (6 mL) was injected, and the reaction solution was stirred for 15 minutes with the benzene inlet closed. The same procedure was repeated once more. 0.215 g of benzene and 21 mL of R-113 were injected in total. 20% Fluorine gas was introduced at the same flow rate for 1 hour, and then nitrogen gas was introduced for 1 hour. The title compound dominated in the product, and the NMR yield was 84%. The product gave the following NMR spectrum data.

$^{19}$F-NMR(376.0 MHz, solvent: CDCl$_3$, standard: CFCl$_3$) δ (ppm): −79.0-81.3(11F), −81.9-82.7(16F), −83.5-86.0 (4F), −86.5-89.0(4F), −129.3(2F), −130.2(4F), −131.9(2F), −145.6(3F).

Example 2-6 Preparation of FCOCF(CF$_3$)O(CF$_2$)$_2$COF by Dissociation of Ester Bonds in a Liquid Phase CF$_3$(CF$_2$)$_2$OCF(CF$_3$)CF$_2$OCF(CF$_3$)COOCF$_2$CF(CF$_3$)O(CF$_2$)$_3$OCOCF(CF$_3$)OCF$_2$CF(CF$_3$)O(CF$_2$)$_2$CF$_3$ (748.25 g) prepared in Example 2-5 was loaded into a flask together with KF powder (3.11 g) and heated at 100° C. on an oil bath with vigorous stirring for 5 hours. A liquid sample (115.23 g) was collected through a reflux condenser adjusted to 90° C. installed above the flask. The title compound was identified as the main component by NMR spectrum analysis. The residue of the reaction residue was further distilled to collect 115.71 g a distillate containing 28% of the title compound. The total yield was 78%.

$^{19}$F-NMR(376 MHz, solvent: CDCl$_3$, standard CFCl$_3$) δ (ppm): 26.6(1F), 25.0(1F), −80.0--80.6(1F), −81.4(3F), −87.7--88.3(1F), −120.3(2F), −130.2(1F).

INDUSTRIAL APPLICABILITY

The process of the present invention enables production of compounds useful as raw materials for fluororesins in high yields in few steps from inexpensive and readily available starting materials. Further, the present invention makes it possible to provide novel useful compounds useful as raw materials for fluororesins.

The entire disclosure of Japanese Patent Application No. 2003-044581 filed on Feb. 21, 2003 including specification, claims and summary is incorporated herein by reference in its entirety.

What is claimed is:

1. A process for producing a compound represented by the following formula (5-4), which comprises reacting a compound represented by the following formula (5-12) with hexafluoropropylene oxide in the presence of a source of fluoride ion, F$^-$, to form a compound represented by the following formula (5-2), pyrolysing the compound represented by the formula (5-2) into a compound represented by the following formula (5-3), and reacting the compound represented by the formula (5-3) with methanol:

FCO(CF$_2$)$_2$O(CF$_2$)$_2$COF     (5-12),

FCOCF(CF$_3$)O(CF$_2$)$_3$O(CF$_2$)$_2$COF     (5-2),

CF$_2$=CFO(CF$_2$)$_3$O(CF$_2$)$_2$COF     (5-3),

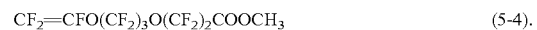

CF$_2$=CFO(CF$_2$)$_3$O(CF$_2$)$_2$COOCH$_3$     (5-4).

2. The process according to claim 1, wherein the compound represented by the formula (5-12) is obtained by a process comprising reacting the following compound (1) and the following compound (2) to form the following compound (3), fluorinating the compound (3) in a liquid phase to form the following compound (4), and then dissociating the ester bond in the compound (4) to form a compound (5), or a compound (5) and a compound (6):

HOCH$_2$-Q-O—(CH$_2$)$_3$—OH     (1),

R$^B$COX     (2),

R$^B$COOCH$_2$-Q-O—(CH$_2$)$_3$—OCOR$^B$     (3),

R$^{BF}$COOCF$_2$-Q$^F$-O—(CF$_2$)$_3$—OCOR$^{BF}$     (4)

FCO-Q$^F$-O—(CF$_2$)$_2$—COF     (5),

R$^{BF}$COF     (6), wherein
- Q: —CH(CH$_3$)— or —CH$_2$CH$_2$—,
- Q$^F$: —CF(CF$_3$)— or —CF$_2$CF$_2$—,
- X: a halogen atom,
- R$^B$: a fluorine-containing monovalent organic group,
- B$^{FB}$: the same group as R$^B$, or a group obtained by fluorination of R$^B$.

3. The process according to claim 1, wherein the source of fluoride ion is an alkali metal fluoride.

4. The process according to claim 3, wherein the alkali metal fluoride is CsF.

5. The process according to claim 2, wherein the source of fluoride ion is an alkali metal fluoride.

6. The process according to claim 5, wherein the alkali metal fluoride is CsF.

* * * * *

UNITED STATES PATENT AND TRADEMARK OFFICE
CERTIFICATE OF CORRECTION

PATENT NO.         : 7,301,052 B2
APPLICATION NO. : 11/206915
DATED              : November 27, 2007
INVENTOR(S)        : Shu-zhong Wang et al.

It is certified that error appears in the above-identified patent and that said Letters Patent is hereby corrected as shown below:

On the title page, Item (73), the Assignee information is incorrect. Item (73) should read:

-- (73) Assignee:   Asahi Glass Company, Limited, Tokyo (JP) --

Signed and Sealed this

Twenty-fifth Day of March, 2008

JON W. DUDAS
*Director of the United States Patent and Trademark Office*